US010286205B2

(12) United States Patent
Steinke et al.

(10) Patent No.: US 10,286,205 B2
(45) Date of Patent: May 14, 2019

(54) SYSTEMS AND METHODS FOR MAKING AND USING IMPROVED CONTACT ARRAYS FOR ELECTRICAL STIMULATION SYSTEMS

(71) Applicant: Boston Scientific Neuromodulation Corporation, Valencia, CA (US)

(72) Inventors: G. Karl Steinke, Valencia, CA (US); Joshua Dale Howard, Winnetka, CA (US); Geoffrey Abellana Villarta, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 231 days.

(21) Appl. No.: 15/011,350

(22) Filed: Jan. 29, 2016

(65) Prior Publication Data

US 2016/0228692 A1    Aug. 11, 2016

Related U.S. Application Data

(60) Provisional application No. 62/113,291, filed on Feb. 6, 2015.

(51) Int. Cl.
*A61N 1/05* (2006.01)
*A61N 1/375* (2006.01)

(52) U.S. Cl.
CPC ............ *A61N 1/05* (2013.01); *A61N 1/3752* (2013.01); *A61N 1/0551* (2013.01)

(58) Field of Classification Search
CPC .. A61N 1/0531; A61N 1/0534; A61N 1/3754; A61N 1/05; A61N 1/3752; A61N 1/0551
See application file for complete search history.

(56) References Cited

U.S. PATENT DOCUMENTS

| 4,602,624 A | 7/1986 | Naples et al. |
| 4,630,611 A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 62/077,762, filed Nov. 10, 2014.

(Continued)

*Primary Examiner* — Michael J D Abreu
(74) *Attorney, Agent, or Firm* — Lowe Graham Jones PLLC; Bruce E. Black

(57) ABSTRACT

An electrical stimulation lead includes a lead body that defines an alignment feature extending distally from a proximal end of the lead body and inwardly from an outer surface of the lead body. The lead also includes electrodes disposed along the distal portion of the lead body, segmented terminals disposed along the proximal portion of the lead and arranged in sets of segmented terminals, and lead conductors electrically coupling the electrodes to the terminals. Each set of segmented terminals includes at least two segmented terminals disposed in a circumferential arrangement at a same longitudinal position of the lead. A system can include the lead and a connector for receiving the proximal end of the lead. The connector can include an alignment protuberance extending into a connector lumen and configured to be received into the alignment groove of the lead to align the lead with the connector.

20 Claims, 12 Drawing Sheets

(56) References Cited

U.S. PATENT DOCUMENTS

| | | | |
|---|---|---|---|
| 4,744,370 A | 5/1988 | Harris | |
| 5,000,194 A | 3/1991 | van den Honert et al. | |
| 5,082,453 A | 1/1992 | Stutz | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,181,969 B1 | 1/2001 | Gord | |
| 6,249,708 B1 * | 6/2001 | Nelson | A61N 1/056 607/122 |
| 6,322,559 B1 | 11/2001 | Daulton et al. | |
| 6,510,347 B2 | 1/2003 | Borkan | |
| 6,516,227 B1 | 2/2003 | Meadows et al. | |
| 6,556,873 B1 | 4/2003 | Smits | |
| 6,564,078 B1 | 5/2003 | Marino et al. | |
| 6,609,029 B1 | 8/2003 | Mann et al. | |
| 6,609,032 B1 | 8/2003 | Woods et al. | |
| 6,678,564 B2 | 1/2004 | Ketterl et al. | |
| 6,741,892 B1 | 5/2004 | Meadows et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,203,548 B2 | 4/2007 | Whitehurst et al. | |
| 7,244,150 B1 | 7/2007 | Brase et al. | |
| 7,292,890 B2 | 11/2007 | Whitehurst et al. | |
| 7,437,193 B2 | 10/2008 | Parramon et al. | |
| 7,450,997 B1 | 11/2008 | Pianca et al. | |
| 7,489,971 B1 | 2/2009 | Franz | |
| 7,668,601 B2 | 2/2010 | Hegland et al. | |
| 7,672,734 B2 | 3/2010 | Anderson et al. | |
| 7,761,165 B1 | 7/2010 | He et al. | |
| 7,761,985 B2 | 7/2010 | Hegland et al. | |
| 7,783,359 B2 | 8/2010 | Meadows | |
| 7,792,590 B1 | 9/2010 | Pianca et al. | |
| 7,803,021 B1 | 9/2010 | Brase | |
| 7,809,446 B2 | 10/2010 | Meadows | |
| 7,822,482 B2 | 10/2010 | Gerber | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,949,395 B2 | 5/2011 | Kuzma | |
| 7,974,705 B2 | 7/2011 | Zdeblick et al. | |
| 7,974,706 B2 | 7/2011 | Moffitt et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,065,008 B2 * | 11/2011 | Sommer | A61N 1/3752 607/37 |
| 8,099,177 B2 | 1/2012 | Dahlberg | |
| 8,175,710 B2 | 5/2012 | He | |
| 8,224,450 B2 | 7/2012 | Brase | |
| 8,225,504 B2 | 7/2012 | Dye et al. | |
| 8,271,094 B1 | 9/2012 | Moffitt et al. | |
| 8,295,944 B2 | 10/2012 | Howard et al. | |
| 8,321,025 B2 | 11/2012 | Bedenbaugh | |
| 8,359,107 B2 | 1/2013 | Pianca et al. | |
| 8,364,278 B2 | 1/2013 | Pianca et al. | |
| 8,391,985 B2 | 3/2013 | McDonald | |
| 8,583,237 B2 | 11/2013 | Bedenbaugh | |
| 8,688,235 B1 | 4/2014 | Pianca et al. | |
| 2001/0023368 A1 | 9/2001 | Black et al. | |
| 2002/0156513 A1 | 10/2002 | Borkan | |
| 2002/0183817 A1 | 12/2002 | Van Venrooij et al. | |
| 2004/0093051 A1 | 5/2004 | Chinn et al. | |
| 2005/0015130 A1 | 1/2005 | Gill | |
| 2005/0038489 A1 | 2/2005 | Grill | |
| 2005/0165465 A1 * | 7/2005 | Pianca | A61N 1/05 607/116 |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0150036 A1 | 6/2007 | Anderson | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 | 10/2008 | Jensen et al. | |
| 2008/0262585 A1 | 10/2008 | Alexander et al. | |
| 2009/0054941 A1 | 2/2009 | Eggen et al. | |
| 2009/0187222 A1 | 7/2009 | Barker | |
| 2009/0204192 A1 | 8/2009 | Carlton et al. | |
| 2009/0276021 A1 | 11/2009 | Meadows et al. | |
| 2010/0030298 A1 | 2/2010 | Martens et al. | |
| 2010/0036468 A1 | 2/2010 | Decre et al. | |
| 2010/0076535 A1 | 3/2010 | Pianca et al. | |
| 2010/0077606 A1 | 4/2010 | Black et al. | |
| 2010/0082076 A1 | 4/2010 | Lee et al. | |
| 2010/0094387 A1 | 4/2010 | Pianca et al. | |
| 2010/0100152 A1 | 4/2010 | Martens et al. | |
| 2010/0268298 A1 | 10/2010 | Moffitt et al. | |
| 2010/0269338 A1 * | 10/2010 | Dye | A61N 1/0531 29/874 |
| 2010/0269339 A1 | 10/2010 | Dye et al. | |
| 2010/0287770 A1 | 11/2010 | Dadd et al. | |
| 2011/0004267 A1 | 1/2011 | Meadows | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0077699 A1 | 3/2011 | Swanson et al. | |
| 2011/0078900 A1 | 4/2011 | Pianca et al. | |
| 2011/0082516 A1 | 4/2011 | Kast et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0238129 A1 | 9/2011 | Moffitt et al. | |
| 2011/0245903 A1 | 10/2011 | Schulte et al. | |
| 2011/0301665 A1 | 12/2011 | Mercanzini et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt | |
| 2012/0203320 A1 | 8/2012 | DiGiore et al. | |
| 2012/0203321 A1 | 8/2012 | Moffitt et al. | |
| 2012/0316615 A1 | 12/2012 | DiGiore et al. | |
| 2013/0105071 A1 | 5/2013 | DiGiore et al. | |
| 2013/0109254 A1 * | 5/2013 | Klardie | A61N 1/0534 439/887 |
| 2013/0197424 A1 | 8/2013 | Bedenbaugh | |
| 2013/0197602 A1 | 8/2013 | Pianca et al. | |
| 2013/0261684 A1 | 10/2013 | Howard | |
| 2013/0317587 A1 | 11/2013 | Barker | |
| 2013/0325091 A1 | 12/2013 | Pianca et al. | |
| 2014/0039587 A1 | 2/2014 | Romero | |
| 2014/0088666 A1 | 3/2014 | Goetz et al. | |
| 2014/0142671 A1 | 5/2014 | Moffitt et al. | |
| 2014/0180375 A1 | 6/2014 | Pianca et al. | |
| 2014/0353001 A1 | 12/2014 | Romero et al. | |
| 2014/0358207 A1 | 12/2014 | Romero | |
| 2014/0358208 A1 * | 12/2014 | Howard | A61N 1/0534 607/116 |
| 2014/0358209 A1 | 12/2014 | Romero et al. | |
| 2014/0358210 A1 | 12/2014 | Howard et al. | |
| 2015/0018909 A1 | 1/2015 | Rebentisch et al. | |

(56) References Cited

U.S. PATENT DOCUMENTS

| | | |
|---|---|---|
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0151113 A1 | 6/2015 | Govea et al. |
| 2015/0360023 A1 | 12/2015 | Howard et al. |
| 2015/0374978 A1 | 12/2015 | Howard et al. |
| 2016/0059019 A1 | 3/2016 | Malinowski et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 62/077,784, filed Nov. 10, 2014.
International Search Report and Written Opinion for PCT/US2016/015823 dated Jun. 16, 2016.

* cited by examiner

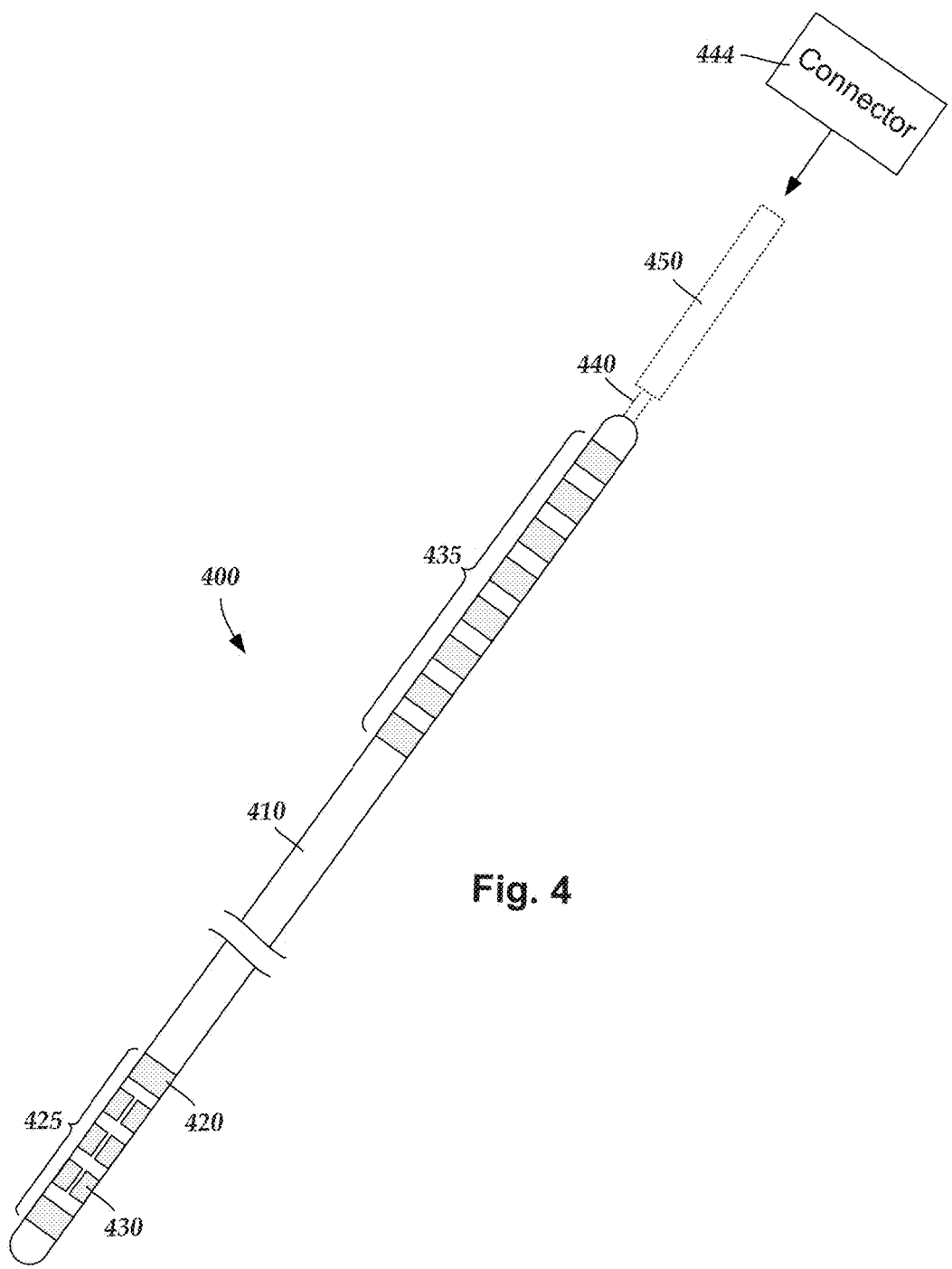

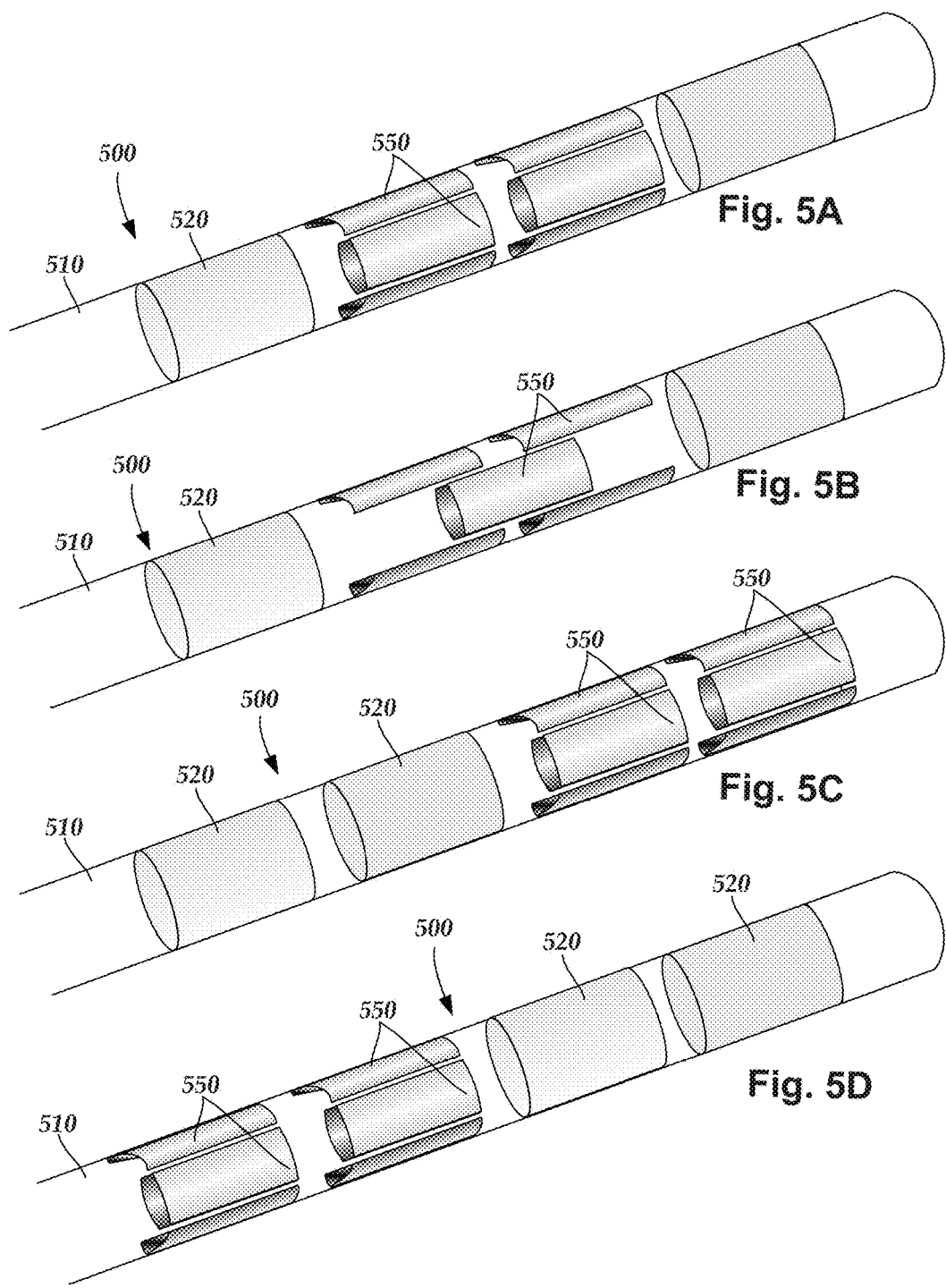

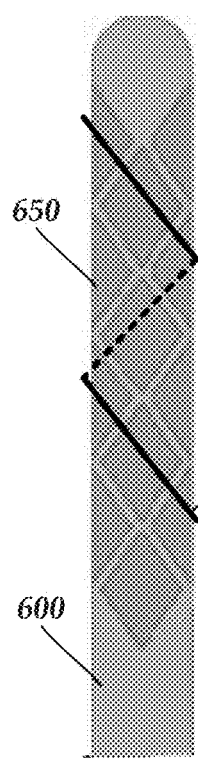
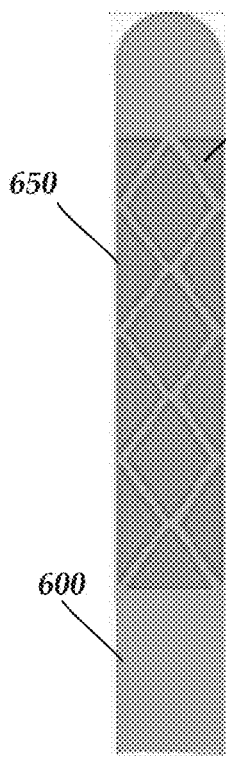
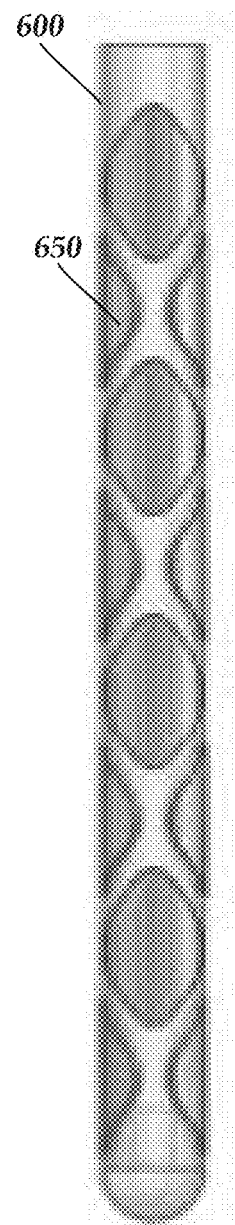
Fig. 6A    Fig. 6B
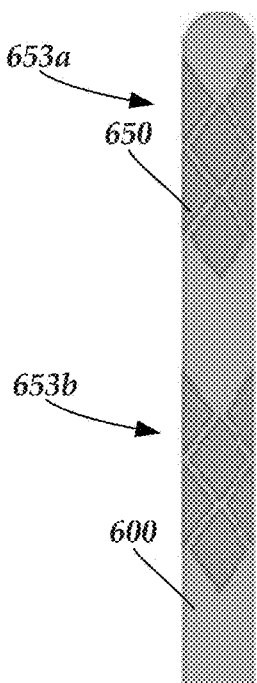
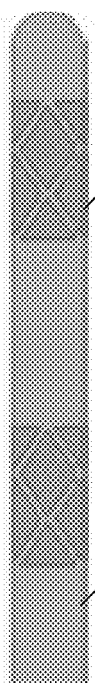
Fig. 6C  Fig. 6D
Fig. 7

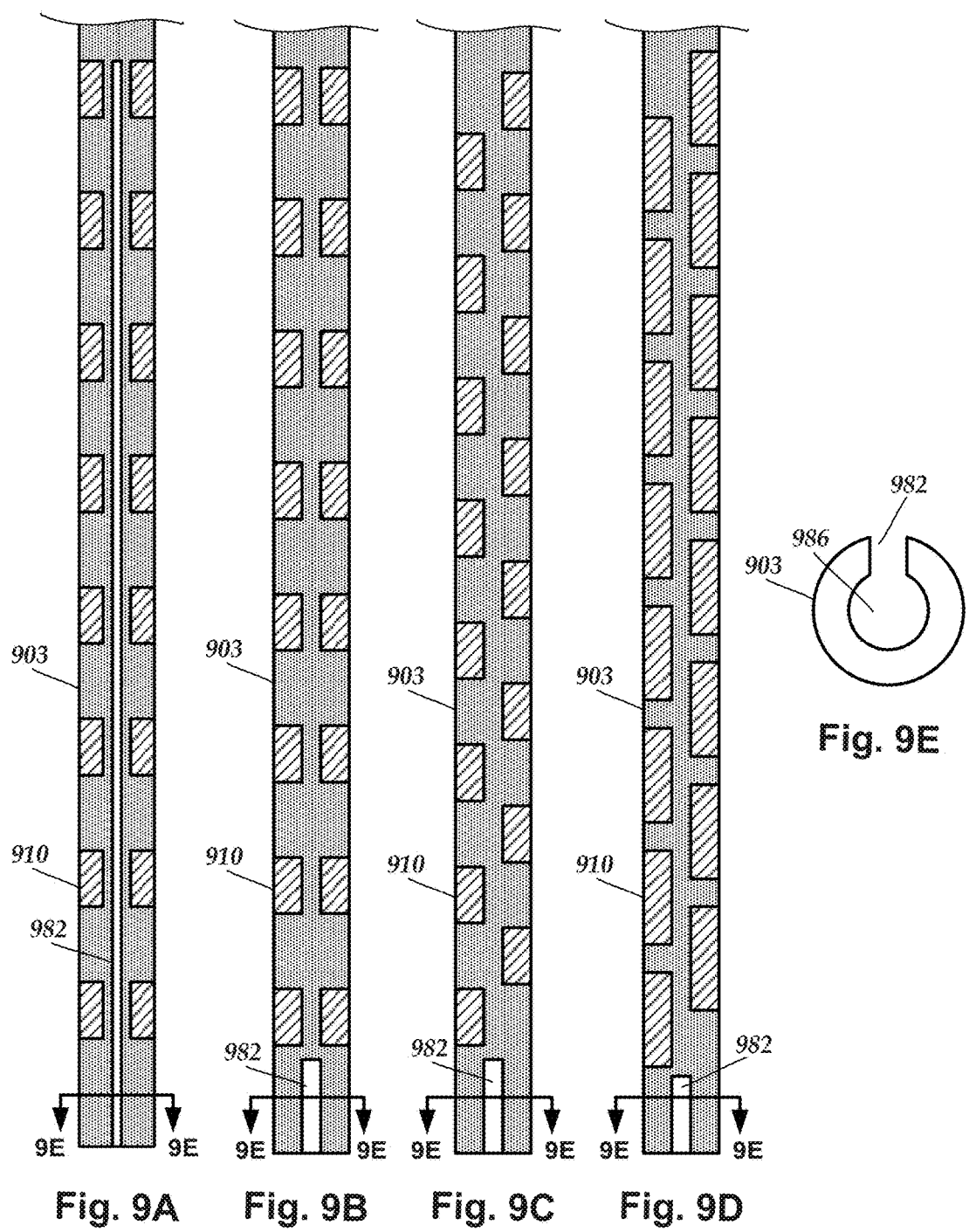

SYSTEMS AND METHODS FOR MAKING AND USING IMPROVED CONTACT ARRAYS FOR ELECTRICAL STIMULATION SYSTEMS

CROSS-REFERENCE TO RELATED APPLICATIONS

This application claims the benefit under 35 U.S.C. § 119(e) of U.S. Provisional Patent Application Ser. No. 62/113,291, filed Feb. 6, 2015, which is incorporated herein by reference.

FIELD

The present invention is directed to the area of implantable electrical stimulation systems and methods of making and using the systems. The present invention is also directed to implantable electrical stimulation systems having elongated members with improved contact arrays, as well as methods of making and using the elongated devices, contact arrays, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation lead including a lead body having an outer surface, a proximal end, a proximal portion, at least one distal portion, an outer surface, a perimeter, and a longitudinal length. The lead body defines an alignment groove extending distally from the proximal end of the lead body and extending inwardly from the outer surface of the lead body. The lead also includes electrodes disposed along the distal portion of the lead body, segmented terminals disposed along the proximal portion of the lead and arranged in sets of segmented terminals, and lead conductors electrically coupling the electrodes to the terminals. Each set of segmented terminals includes at least two of the segmented terminals disposed in a circumferential arrangement at a same longitudinal position of the lead. Each segmented terminal extends around less than the entire perimeter of the lead and is separated from all other segmented terminals by portions of the lead body.

In at least some embodiments, the alignment groove terminates proximal to any of the segmented terminals. In at least some embodiments, the alignment groove extends between at least two of the segmented terminals of at least one of the sets of segmented terminals. In at least some embodiments, the alignment groove extends between at least two of the segmented terminals of each of the sets of segmented terminals. In at least some embodiments, each of the sets of segmented terminals contains exactly two segmented terminals. In at least some embodiments, the lead body further defines a central lumen along the lead body and configured and arranged to receive a stylet, where the alignment groove extends inwardly from the outer surface of the lead body to the central lumen.

Another embodiment is an electrical stimulation system that includes any of the electrical stimulation leads described above; and a connector defining a connector lumen configured and arranged to receive the proximal end of the electrical stimulation lead. The connector includes segmented connector contacts disposed along the connector lumen and arranged in sets of segmented connector contacts. Each set of segmented connector contacts includes at least two of the segmented connector contacts disposed in a circumferential arrangement at a same longitudinal position along the connector lumen.

In at least some embodiments, the system also includes a control module that includes the connector, a housing, and an electrical subassembly disposed in the housing and electrical coupled to the connector contacts of the connector. In at least some embodiments, the system also includes a lead extension that includes the connector. In at least some embodiments, each of the segmented connector contacts includes a leaf spring. In at least some embodiments, each of the segmented connector contacts includes a coiled leaf spring. In at least some embodiments, the connector further includes an alignment protuberance extending into the connector lumen and disposed at least at an opening into the connector lumen, where the alignment groove of the lead is configured and arranged to receive the alignment protuberance to align the lead with the connector.

Yet another embodiment is an electrical stimulation system including a connector defining a connector lumen configured and arranged to receive the proximal end of the electrical stimulation lead. The connector includes a connector housing containing the connector lumen and defining an opening into the connector lumen, segmented connector contacts disposed within the connector housing and along the connector lumen and arranged in sets of segmented connector contacts, and an alignment protuberance extending into the connector lumen and disposed at least at the opening into the connector lumen. Each set of segmented connector contacts includes at least two of the segmented connector contacts disposed in a circumferential arrangement at a same longitudinal position along the connector lumen. Each of the segmented connector contacts includes a leaf spring.

In at least some embodiments, the leaf spring is a coiled leaf spring. In at least some embodiments the system also includes a control module, where the control module includes the connector, a housing, and an electrical subassembly disposed in the housing and electrical coupled to the connector contacts of the connector. In at least some embodiments the system also includes a lead extension, where the lead extension includes the connector.

In at least some embodiments, the system also includes a lead, the lead including a lead body having an outer surface, a proximal end, a proximal portion, at least one distal portion, an outer surface, a perimeter, and a longitudinal length with the lead body further defining an alignment groove extending distally from the proximal end of the lead body and extending inwardly from the outer surface of the lead body; electrodes disposed along the distal portion of the lead body, terminals disposed along the proximal portion of the lead, and lead conductors electrically coupling the electrodes to the terminals. In at least some embodiments, terminals are segmented terminals disposed along the proximal portion of the lead and arranged in sets of segmented terminals, where each set of segmented terminals includes at least two of the segmented terminals disposed in a circumferential arrangement at a same longitudinal position of the lead, where each segmented terminals extends around less than the entire perimeter of the lead and is separated from all other segmented terminals by portions of the lead body. In at least some embodiments, the alignment groove terminates proximal to any of the segmented terminals. In at least some embodiments, the alignment groove extends between at least two of the segmented terminals of at least one of the sets of segmented terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4 is a schematic side view of yet another embodiment of an implantable medical device for brain stimulation, according to the invention;

FIG. 5A is a schematic perspective view of one embodiment of a distal end of a lead containing segmented electrodes, according to the invention;

FIG. 5B is a schematic perspective view of a second embodiment of a distal end of a lead containing segmented electrodes, according to the invention;

FIG. 5C is a schematic perspective view of a third embodiment of a distal end of a lead containing segmented electrodes, according to the invention;

FIG. 5D is a schematic perspective view of a fourth embodiment of a distal end of a lead containing segmented electrodes, according to the invention;

FIG. 6A is a schematic side view of an eighth embodiment of a distal end of a lead containing segmented electrodes, according to the invention;

FIG. 6B is a schematic side view of a ninth embodiment of a distal end of a lead containing segmented electrodes, according to the invention;

FIG. 6C is a schematic side view of a tenth embodiment of a distal end of a lead containing segmented electrodes, according to the invention;

FIG. 6D is a schematic side view of an eleventh embodiment of a distal end of a lead containing segmented electrodes, according to the invention;

FIG. 7 is a schematic side view of a twelfth embodiment of a distal end of a lead containing segmented electrodes, according to the invention;

FIG. 9A is a schematic side view of one embodiment of a distal end of a lead containing segmented electrodes and an alignment groove, according to the invention;

FIG. 9B is a schematic side view of a second embodiment of a distal end of a lead containing segmented electrodes and an alignment groove, according to the invention;

FIG. 9C is a schematic side view of a third embodiment of a distal end of a lead containing segmented electrodes and an alignment groove, according to the invention;

FIG. 9D is a schematic side view of a fourth embodiment of a distal end of a lead containing segmented electrodes and an alignment groove, according to the invention;

FIG. 9E is a schematic cross-sectional view of any one of the leads of FIGS. 9A-9D, according to the invention;

DETAILED DESCRIPTION

The present invention is directed to the area of implantable electrical stimulation systems and methods of making and using the systems. The present invention is also directed to implantable electrical stimulation systems having elongated members with improved contact arrays, as well as methods of making and using the elongated devices, contact arrays, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference.

Figure 1:
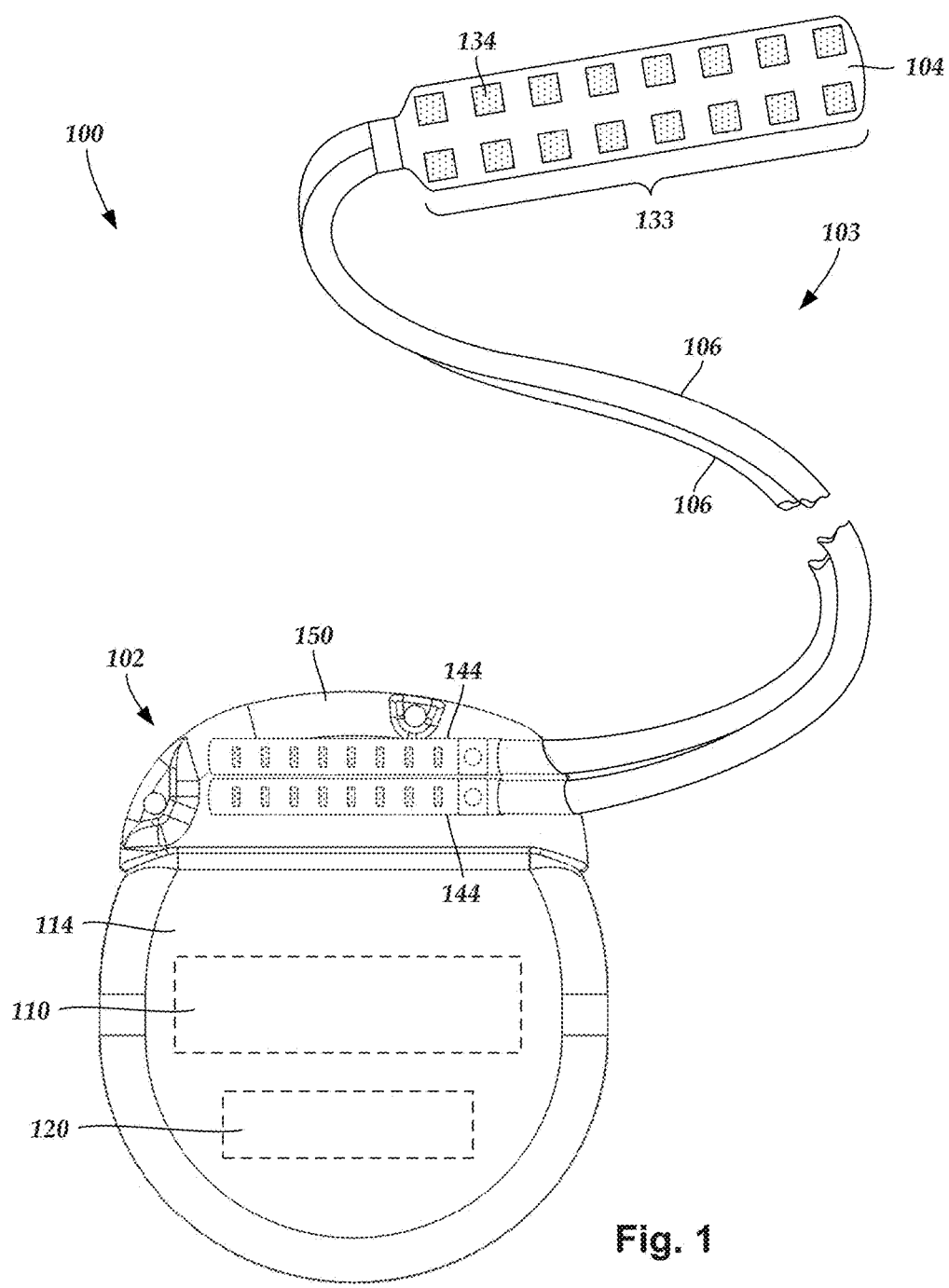
FIG. 1 is a schematic view of one embodiment of an implantable medical device that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connectors 144 into which the proximal end of the one or more lead bodies 106 can be plugged to make an electrical connection via connector contacts (e.g., 316 in FIG. 3A) disposed in the connector 144 and terminals (e.g., 310 in FIG. 3A) on each of the one or more lead bodies 106. The connector contacts are coupled to the electronic subassembly 110 and the terminals are coupled to the electrodes 134. In FIG. 1, two connectors 144 are shown.

The one or more connectors 144 may be disposed in a header 150. The header 150 provides a protective covering over the one or more connectors 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
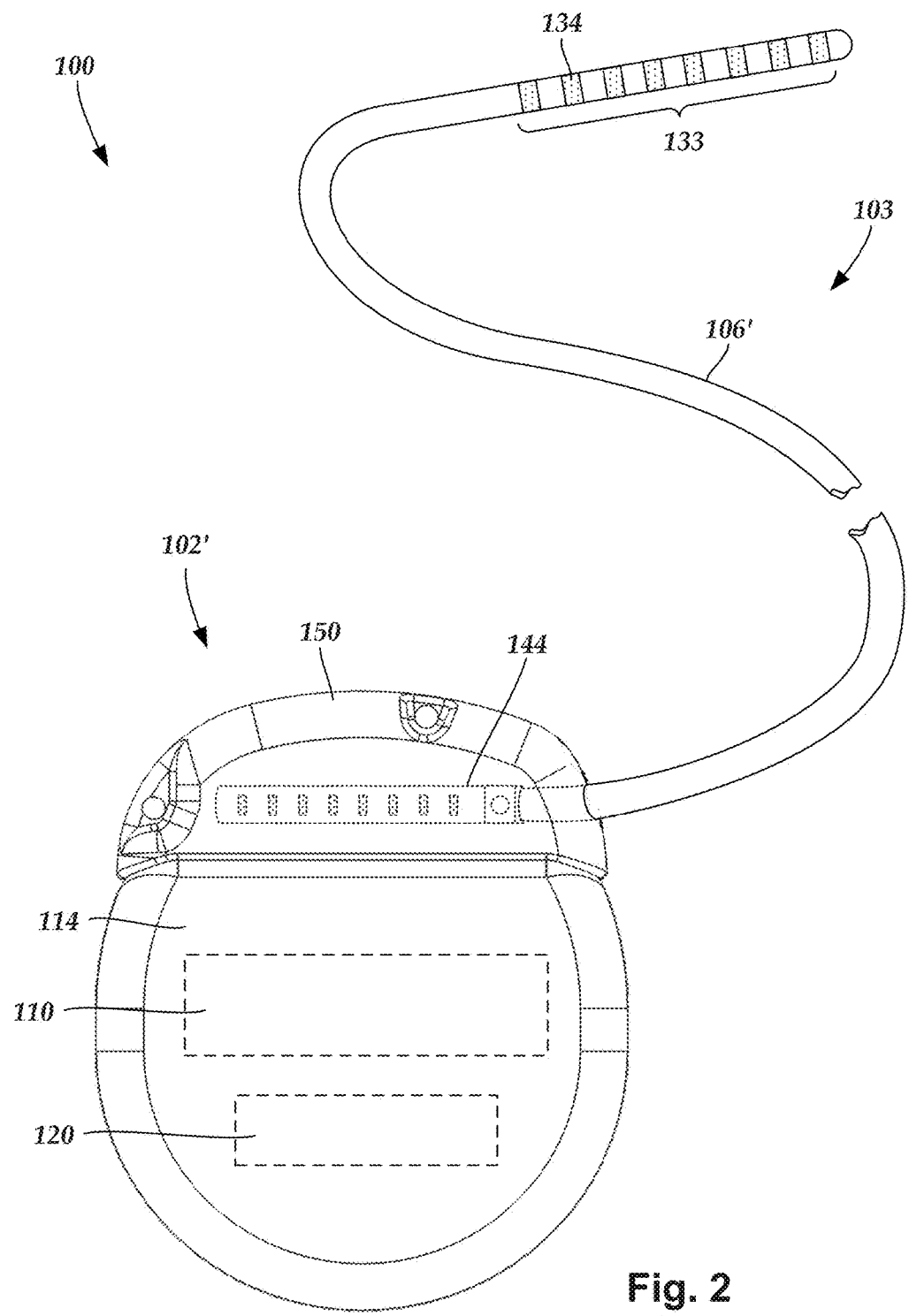
FIG. 2 is a schematic view of another embodiment of an implantable medical device that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connectors (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connectors 144 disposed on the control module 102. The control module 102 can include any suitable number of connectors 144 including, for example, two three, four, five, six, seven, eight, or more connectors 144. It will be understood that other numbers of connectors 144 may be used instead. In FIG. 1, each of the two lead bodies 106 includes eight terminals that are shown coupled with eight conductive contacts disposed in a different one of two different connectors 144.

Figure 3A:
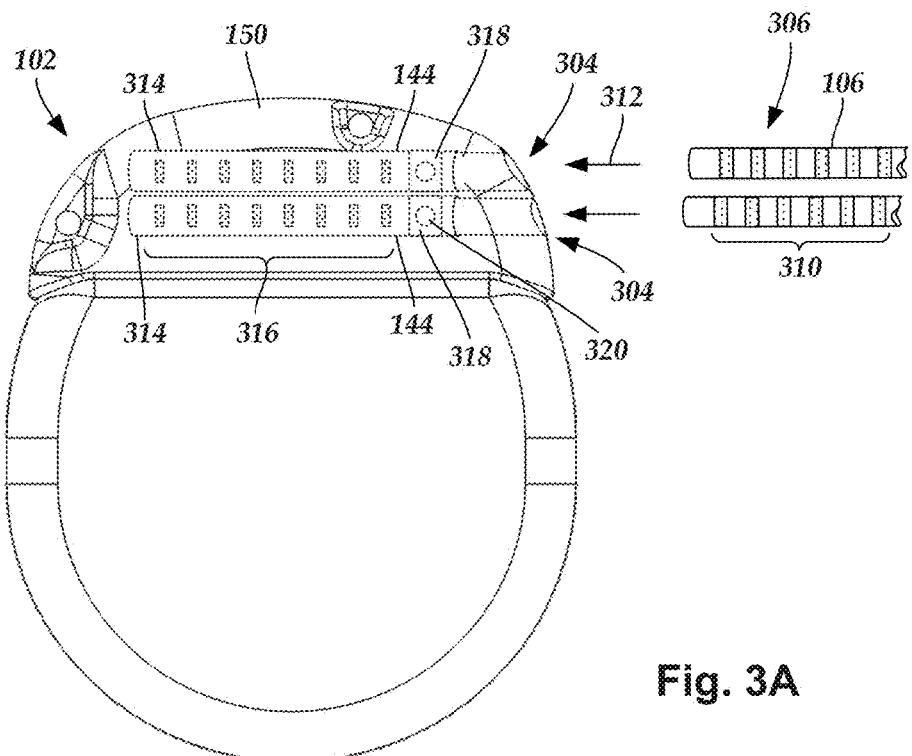
FIG. 3A is a schematic view of one embodiment of a plurality of connectors disposed in the control module of FIG. 1, the connectors configured and arranged to receive the proximal portions of the lead bodies of FIG. 1, according to the invention.
Figure 3B:
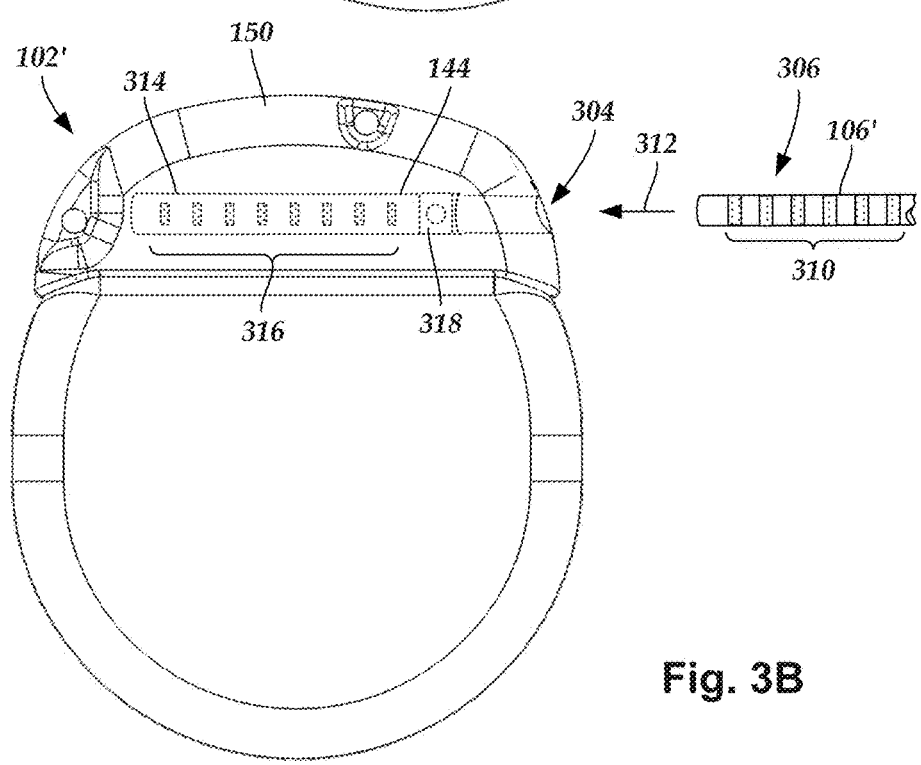
FIG. 3B is a schematic view of one embodiment of a connector disposed in the control module of FIG. 2, the connector configured and arranged to receive the proximal portion of one of the lead body of FIG. 2, according to the invention.

FIG. 3A is a schematic side view of one embodiment of a plurality of connectors 144 disposed on the control module 102. In at least some embodiments, the control module 102 includes two connectors 144. In at least some embodiments, the control module 102 includes four connectors 144. In FIG. 3A, proximal ends 306 of the plurality of lead bodies 106 are shown configured and arranged for insertion to the control module 102. FIG. 3B is a schematic side view of one embodiment of a single connector 144 disposed on the control module 102'. In FIG. 3B, the proximal end 306 of the single lead body 106' is shown configured and arranged for insertion to the control module 102'.

In FIGS. 3A and 3B, the one or more connectors 144 are disposed in the header 150. In at least some embodiments, the header 150 defines one or more lumens 304 into which the proximal end(s) 306 of the one or more lead bodies 106/106' with terminals 310 can be inserted, as shown by directional arrows 312, in order to gain access to the connector contacts disposed in the one or more connectors 144.

The one or more connectors 144 each include a connector housing 314 and a plurality of connector contacts 316 disposed therein. Typically, the connector housing 314 provides access to the plurality of connector contacts 316 via the lumen 304. In at least some embodiments, one or more of the connectors 144 further includes a retaining element 318 configured and arranged to fasten the corresponding lead body 106/106' to the connector 144 when the lead body 106/106' is inserted into the connector 144 to prevent undesired detachment of the lead body 106/106' from the connector 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more lumens 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connectors in control modules are found in, for example, U.S. Pat. Nos. 7,244,150 and 8,224,450, which are incorporated by reference.

Figure 3C:
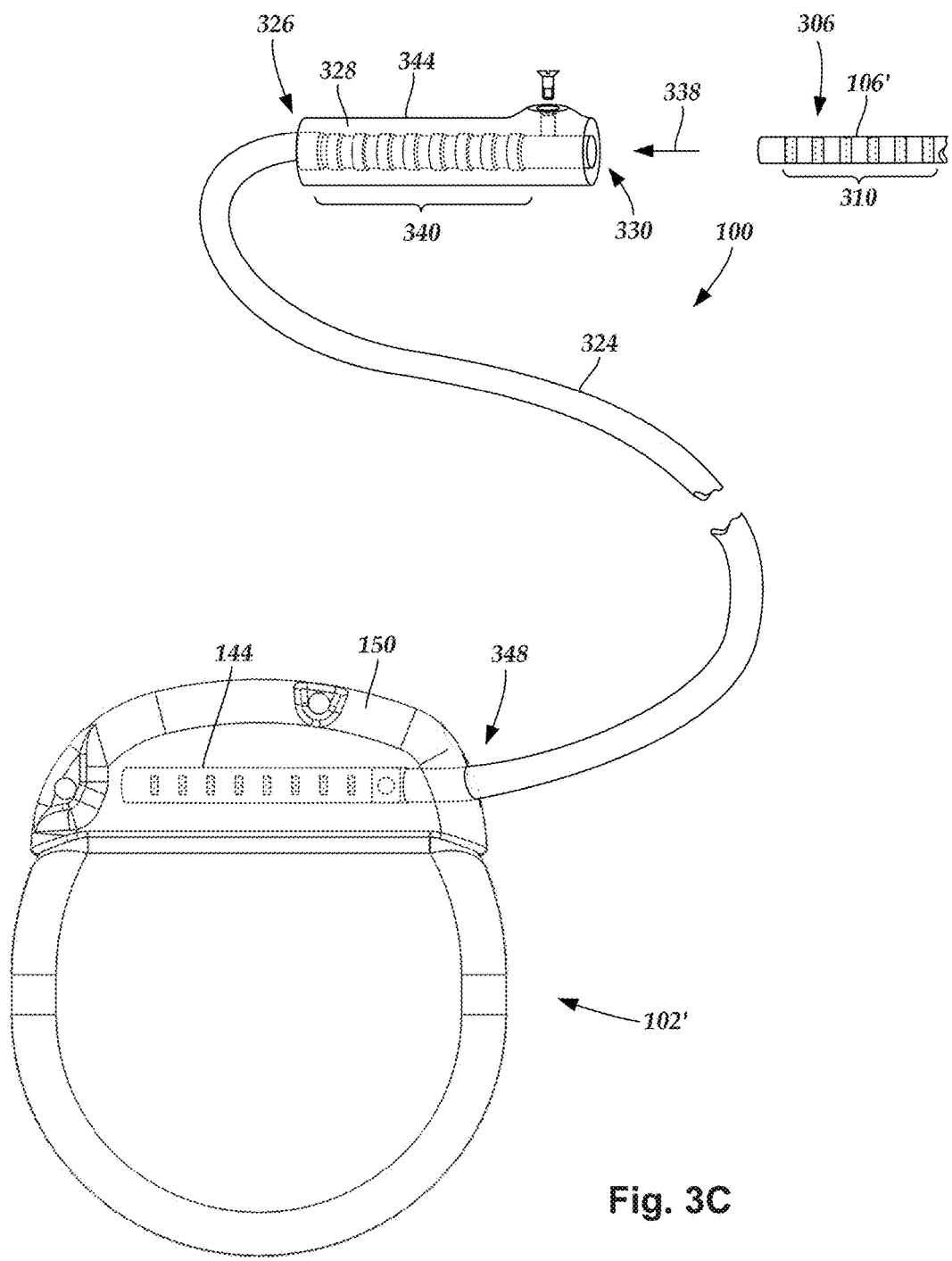
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector 322 is disposed on a lead extension 324. The lead extension connector 322 is shown disposed at a distal end 326 of the lead extension 324. The lead extension connector 322 includes a connector housing 344. The connector housing 344 defines at least one lumen 330 into which a proximal end 306 of the lead body 106' with terminals 310 can be inserted, as shown by directional arrow 338. The lead extension connector 322 also includes a plurality of connector contacts 340. When the lead body 106' is inserted into the lumen 330, the connector contacts 340 disposed in the connector housing 344 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector disposed in another lead extension. In other embodiments (as shown in FIG. 3C), the proximal end 348 of the lead extension 324 is configured and arranged for insertion into the connector 144 disposed on the control module 102'.

It will be understood that the control modules 102/102' can receive either lead bodies 106/106' or lead extensions 324. It will also be understood that the electrical stimulation system 100 can include a plurality of lead extensions 324. For example, each of the lead bodies 106 shown in FIGS. 1 and 3A can, alternatively, be coupled to a different lead extension 324 which, in turn, are each coupled to different ports of a two-port control module, such as the control module 102 of FIGS. 1 and 3A.

Turning to FIG. 4, in the case of deep brain stimulation, the lead may include stimulation electrodes, recording electrodes, or a combination of both. At least some of the stimulation electrodes, recording electrodes, or both are provided in the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

FIG. 4 illustrates one embodiment of a device 400 for brain stimulation. The device includes a lead 410, a plurality of electrodes 425 disposed at least partially about a perimeter of the lead 410, a plurality of terminals 435, a connector 444 for connection of the electrodes to a control unit, and a stylet 440 for assisting in insertion and positioning of the lead in the patient's brain. The stylet 440 can be made of a rigid material. Examples of suitable materials for the stylet include, but are not limited to, tungsten, stainless steel, and plastic. The stylet 440 may have a handle 450 to assist insertion into the lead 410, as well as rotation of the stylet 440 and lead 410. The connector 444 fits over a proximal end of the lead 410, preferably after removal of the stylet 440.

In FIG. 4, the electrodes 425 are shown as including both ring electrodes, such as ring electrode 420, and segmented electrodes, such as segmented electrodes 430. In some embodiments, the electrodes 425 are all segmented. In other embodiments, the electrodes 425 are all ring-shaped. In FIG. 4, each of the terminals 435 is shown as being ring-shaped. The segmented electrodes of FIG. 4 are shown in sets of two, where the two segmented electrodes of a particular set are electrically isolated from one another and are circumferentially-offset along the lead 410. Any suitable number of segmented electrodes can be formed into a set including, for example, two, three, four, or more segmented electrodes.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue. Examples of leads with segmented electrodes include U.S. Pat. Nos. 8,295,944; and 8,391,985; and U.S. Patent Applications Publication Nos. 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated herein by reference.

Figure 5E:
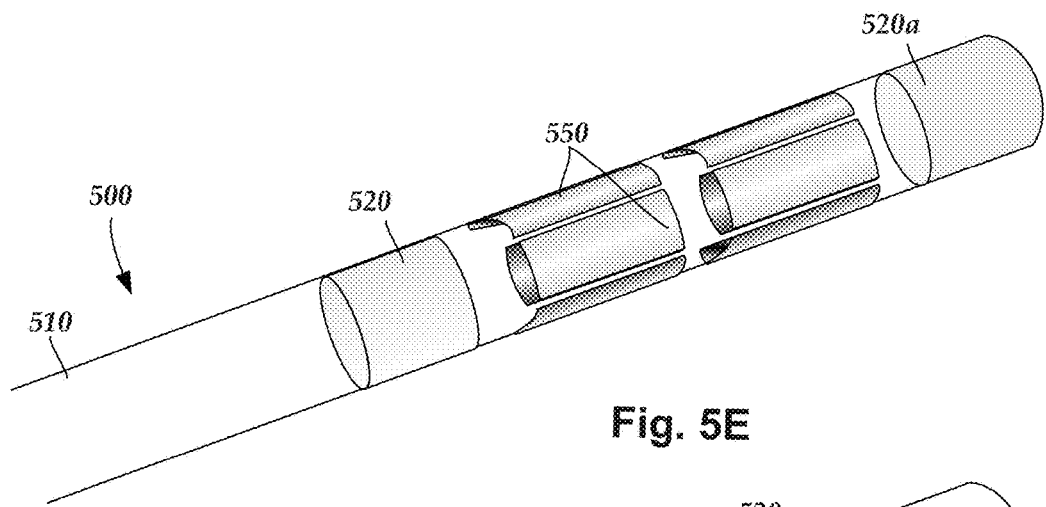
FIG. 5E is a schematic perspective view of a fifth embodiment of a distal end of a lead containing segmented electrodes, according to the invention.
Figure 5F:
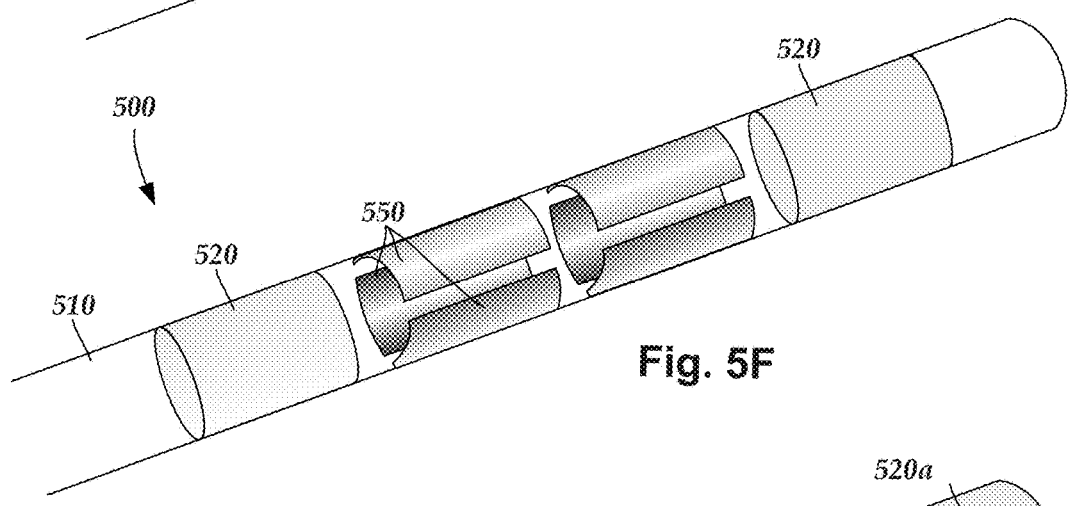
FIG. 5F is a schematic perspective view of a sixth embodiment of a distal end of a lead containing segmented electrodes, according to the invention.

FIGS. 5A-5H illustrate leads 500 with segmented electrodes 550, optional ring electrodes 520 or tip electrodes 520a, and a lead body 510. The sets of segmented electrodes 550 each include either two (FIG. 5B), three (FIGS. 5E-5H), or four (FIGS. 5A, 5C, and 5D) or any other number of segmented electrodes including, for example, three, five, six, or more. The sets of segmented electrodes 550 can be aligned with each other (FIGS. 5A-5G) or staggered (FIG. 5H).

When the lead 500 includes both ring electrodes 520 and segmented electrodes 550, the ring electrodes 520 and the segmented electrodes 550 may be arranged in any suitable configuration. For example, when the lead 500 includes two ring electrodes 520 and two sets of segmented electrodes 550, the ring electrodes 520 can flank the two sets of segmented electrodes 550 (see e.g., FIGS. 1, 5A, and 5E-5H). Alternately, the two sets of ring electrodes 520 can be disposed proximal to the two sets of segmented electrodes 550 (see e.g., FIG. 5C), or the two sets of ring electrodes 520 can be disposed distal to the two sets of segmented electrodes 550 (see e.g., FIG. 5D). One of the ring electrodes can be a tip electrode (see, tip electrode 520a of FIGS. 5E and 5G). It will be understood that other configurations are possible as well (e.g., alternating ring and segmented electrodes, or the like).

By varying the location of the segmented electrodes 550, different coverage of the target neurons may be selected. For example, the electrode arrangement of FIG. 5C may be useful if the physician anticipates that the neural target will be closer to a distal tip of the lead body 510, while the electrode arrangement of FIG. 5D may be useful if the physician anticipates that the neural target will be closer to a proximal end of the lead body 510.

Figure 5G:
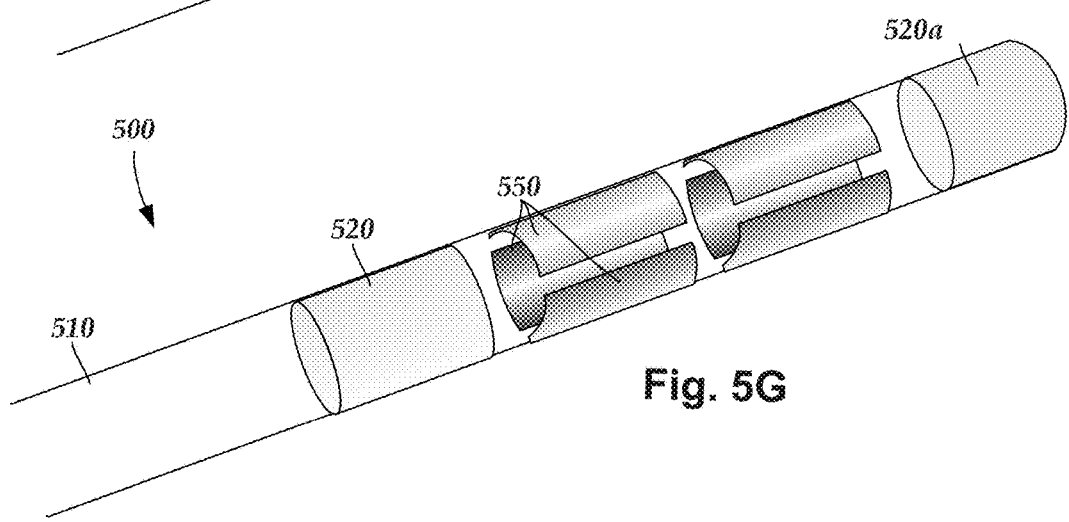
FIG. 5G is a schematic perspective view of a seventh embodiment of a distal end of a lead containing segmented electrodes, according to the invention.

Any combination of ring electrodes 520 and segmented electrodes 550 may be disposed on the lead 500. For example, the lead may include a first ring electrode 520, two sets of segmented electrodes; each set formed of four segmented electrodes 550, and a final ring electrode 520 at the end of the lead. This configuration may simply be referred to as a 1-4-4-1 configuration (FIGS. 5A and 5E—ring electrodes 520 and segmented electrode 550). It may be useful to refer to the electrodes with this shorthand notation. Thus, the embodiment of FIG. 5C may be referred to as a 1-1-4-4 configuration, while the embodiment of FIG. 5D may be referred to as a 4-4-1-1 configuration. The embodiments of FIGS. 5F, 5G, and 5H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 550 are disposed on the lead. The 1-3-3-1 electrode configuration of FIGS. 5F, 5G, and 5H has two sets of segmented electrodes, each set containing three electrodes disposed around the perimeter of the lead, flanked by two ring electrodes (FIGS. 5F and 5H) or a ring electrode and a tip electrode (FIG. 5G). In some embodiments, the lead includes 16 electrodes. Possible configurations for a 16-electrode lead include, but are not limited to 4-4-4-4; 8-8; 5-3-3-3-3-1 (and all rearrangements of this configuration); and 2-2-2-2-2-2-2-2.

FIGS. 6A-7 illustrate alternative arrangements of segmented electrodes 650. In FIG. 6A, the segmented electrodes 650 disposed on lead 600 have a diamond shape and are arranged in an "argyle pattern". In at least some embodiments, the arrangement of electrodes can form a helical pattern as indicated by path 651 (with the dotted portion of the path corresponding to the unviewed side of the lead). In the embodiment illustrated in FIG. 6A, the electrodes form two helical paths. The embodiment of FIG. 6B is similar except that the electrodes 650a at either end of the array are truncated to form a triangular shape. The embodiment of FIG. 7 is similar to that of FIG. 6A except that the corners of the electrodes 650 are rounded instead of sharp.

The embodiments of FIGS. 6C and 6D are similar to those of FIGS. 6A and 6B, respectively, except that the electrodes 650 are arranged in two space-apart arrays 653a, 653b. It will be understood that other electrode configurations can include three, four, or more different arrays of electrodes. Moreover, each of the arrays of electrodes can include the same or different numbers of electrodes. It will also be understood that any of the embodiments of FIGS. 6A-7 can be modified to include one or more ring electrodes, a tip electrode, or any combination thereof. In addition, an embodiment of a lead can include any combination of electrode shapes illustrated in any of the FIGS. 4-7. In other embodiments, the electrodes can have a round shape or any other suitable regular or irregular shape.

Figure 8A:
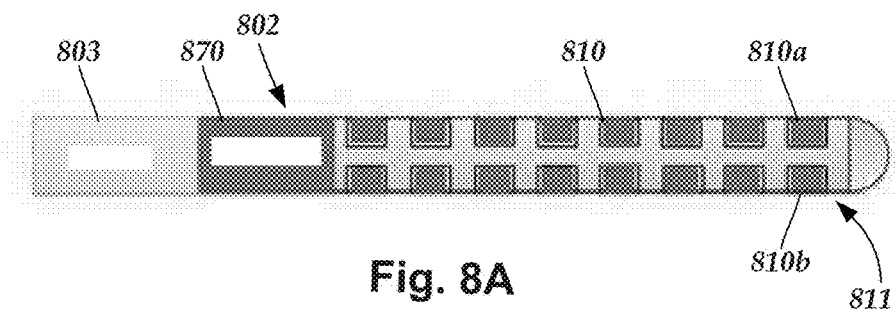
FIG. 8A is schematic side view of one embodiment of a proximal end of a lead containing segmented terminals, according to the invention.

Turning to FIG. 8A, in at least some embodiments it may be advantageous to design an elongate member (e.g., a lead, lead extension, splitter, adaptor, or the like) with segmented terminals. In at least some embodiments, the elongate member also includes segmented electrodes. Utilizing segmented terminals may reduce the physical size of the terminal array when compared to conventional terminal arrays with ring-shaped terminals. Consequently, the portion of the elongate member that is inserted into a connector to make electrical contact with the pulse generator can be reduced, as compared to conventional electrical stimulation systems. Alternately, the number of terminals that can be disposed along a proximal portion of an elongate member and that can be inserted into a conventionally-sized connector may be increased from conventional electrical stimulation systems.

FIG. 8A illustrates, in schematic perspective view, one embodiment of a proximal portion 802 of a lead 803 (or other elongate member) with an array of segmented terminals 810 and an optional retention sleeve 870. The segmented terminals 810 can be formed in sets of two or more terminals at a same position along the longitudinal axis of the lead. Each of the segmented terminals of a particular set extends around less than (for example, no more than 45%, 40%, 33%, 30%, or 25% of) the entire perimeter of the elongate member. The segmented terminals of the set are not in electrical contact with one another and are circumferentially-offset from one another along the elongate member. In at least some embodiments, the terminal array includes at least one segmented terminal set, such as segmented terminal set 811 which, in turn, includes multiple segmented terminals 810, such as segmented terminals 810a and 810b. In some embodiments, a set of segmented terminals can have two, three, four, or more segmented terminals disposed at the same position along the longitudinal axis of the elongate member, but circumferentially offset from each other.

In some embodiments, the terminal array is formed exclusively from segmented terminals. In other embodiments, the terminal array includes a combination of one or more ring-shaped terminals and one or more segmented terminal sets.

The terminal array can include any suitable number of segmented terminal sets 811 including, for example, one, two, three, four, five, six, seven, eight, nine, ten eleven, twelve, thirteen, fourteen, fifteen, sixteen, or more segmented-terminal sets. In FIG. 8A, eight segmented terminal sets 811 are shown disposed along the lead 803.

In at least some embodiments the elongate member includes a single proximal portion and multiple distal portions. One advantage of implementing segmented terminals is that it may increase the number of terminals disposed along a lead from conventional leads. The increased number of terminals may enable the lead to be designed with multiple distal portions, where a different electrode array is disposed along each of the distal portions, and where electrodes of each of the multiple electrode arrays are coupled to terminals disposed along a single proximal portion. Such a design may be useful, for example, in deep brain stimulation where bilateral stimulation may be desirable.

When the lead has multiple distal portions and a single proximal portion with segmented terminals, the single proximal portion can be received by a single connector port. Such an arrangement enables each of multiple electrode arrays disposed along different distal portions to be operated by a single control module. Additionally, such a design enables multiple electrode arrays to be controlled by a single control module via a single connector with a single lead-receiving port.

Figure 8B:
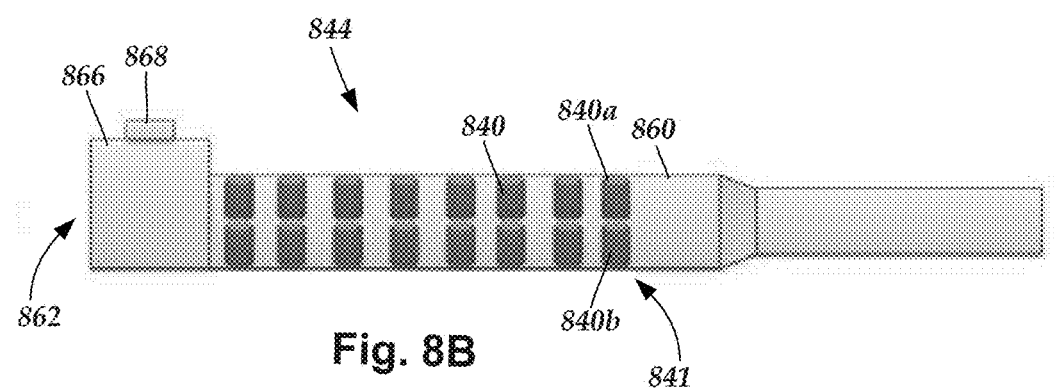
FIG. 8B is schematic side view of one embodiment of a connector containing segmented connector contacts, according to the invention.

Turning to FIG. 8B, the proximal portion of the elongate member, such as the lead 803 (FIG. 8A), is typically inserted into a connector 844 disposed along a lead extension, control module, adaptor, splitter, or the like. In at least some embodiments, a connector 844 suitable for receiving the proximal portion of an elongate member (e.g., the lead 503) with segmented terminals includes connector contact sets having segmented connector contacts 840 suitable for coupling with the segmented terminals.

Figure 8C:
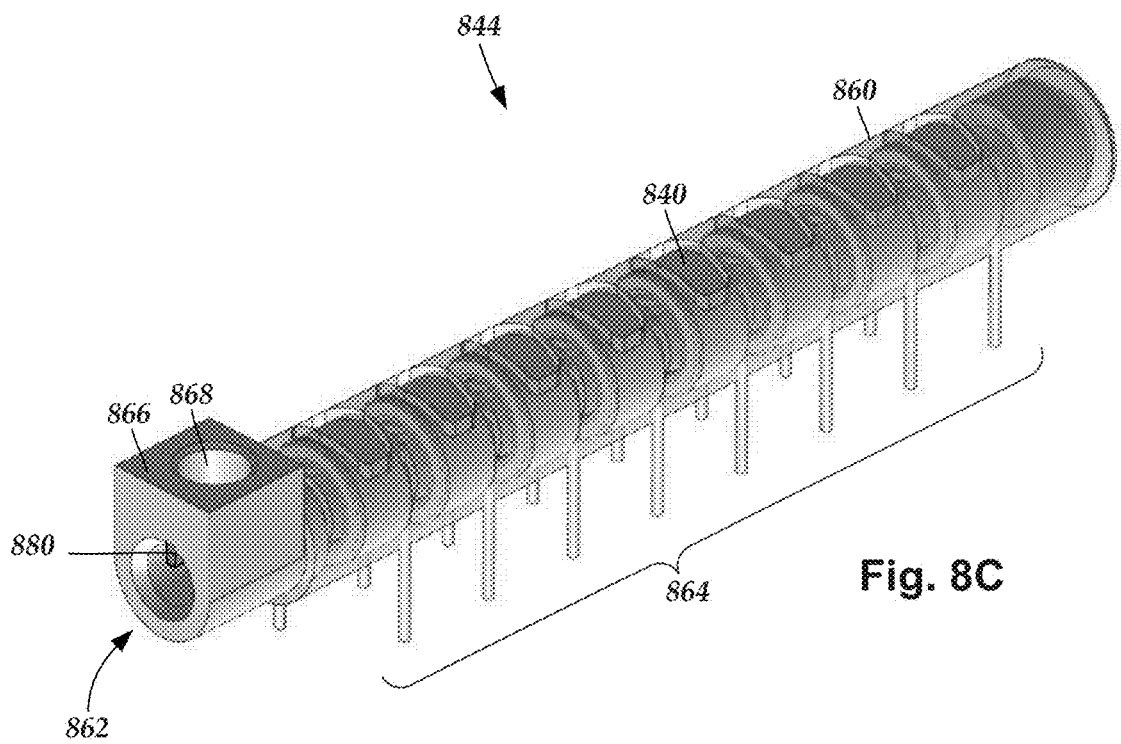
FIG. 8C is schematic perspective view of another embodiment of a connector containing segmented connector contacts, according to the invention.

FIGS. 8B and 8C illustrate embodiments of a connector 844 suitable for receiving the proximal portion 802 of the lead 803. The connector 844 includes an elongated connector housing 860 that defines a connector lumen 862 suitable for receiving a portion of an elongate member, such as the lead 503; a lead extension (e.g., 324 in FIG. 3C); or the like. The connector 844 can also include an alignment protuberance 880 (FIG. 8C—for example, a pin, wall, rod, or rail) that extends into the connector lumen and can be used to align the lead with the connector as described below. It will be recognized that the connector lumen may have one or more open slots extending along part or all of the length of the connector lumen. Although the illustrated connector lumen has a circular cross-section, it will be understood that lumens with other cross-sections (and leads with non-circular cross-sections) can also be used including, but not limited to, oval, square, rectangular, triangular, pentagonal, hexagonal, octagonal, cruciform, or any other suitable regular or irregular cross-sectional shape.

Multiple connector contacts 840 are disposed in a spaced-apart relationship along the longitudinal length of the connector housing 860 such that the connector contacts are exposed to the connector lumen 862 and also to an array of conductive members 864 that couple the connector contacts to other components. When, for example, the connector 844 is disposed on a lead extension (e.g., 324 in FIG. 3C), the conductive members 864 may couple the connector contacts to lead extension terminals. When, for example, the connector 844 is disposed on a control module, the conductive members 864 may couple the connector contacts 840 to the electronic subassembly (110 in FIG. 1). In at least some embodiments, the conductive members 864 couple the connector contacts 840 to the electronic subassembly (110 in FIG. 1) via feedthrough pins extending through the sealed housing (114 in FIG. 1).

The segmented connector contacts 840 can be formed in sets of two or more terminals at a same position along the longitudinal axis of the connector lumen 862. Each of the segmented connector contacts of a particular set extends around less than (for example, no more than 45%, 40%, 33%, 30%, or 25% of) the entire perimeter of the connector lumen. The segmented connector contacts of the set are not in electrical contact with one another and are circumferentially-offset from one another along the connector lumen. In at least some embodiments, the connector contact array includes at least one segmented connector contacts set, such as segmented connector contacts set 841 which, in turn, includes multiple segmented connector contacts 840, such as segmented terminals 840a and 840b. In some embodiments, a set of segmented connector contacts can have two, three, four, or more segmented connector contacts disposed at the same position along the longitudinal axis of the connector lumen, but circumferentially offset from each other.

Optionally, a retention block 866 is disposed along the connector 844. The retention block 866 can be used to facilitate retention of an elongate member when the elongate member is inserted into the connector lumen 862. In at least some embodiments, the retention block 866 defines a fastening aperture 868 configured to receive a fastener (e.g., a set screw, pin, or the like) which can engage the optional retention sleeve 870 (FIG. 8A) of the lead. In at least some embodiments, the fastener, when received by the fastener aperture 868, is configured to tighten against a portion of the elongate member (e.g., a retention sleeve) when the elongate member is inserted into the connector lumen 862.

Because there are multiple segmented terminals 810 and segmented connector contacts 840 at the same longitudinal positions along the lead 803 and connector 844, in at least some embodiments, it is important to ensure proper alignment between the connector 844 and the lead 803 (or other elongate member) so that each terminal is electrically connected to a single connector contact. FIGS. 9A and 9E illustrate a lead 903 with an alignment groove 982 formed along a portion of the proximal end of the lead. FIGS. 9B, 9C, and 9D illustrate alternative embodiments of the lead 903 and the alignment groove 982. In addition, FIGS. 9C and 9D illustrate arrangements of segmented terminals 910 in longitudinal columns that are longitudinally offset from each other (for example, the terminals on the left of FIGS. 9C and 9D are longitudinally offset from those on the right). In FIG. 9C the terminals of different longitudinal columns do not overlap and in FIG. 9D the terminals of different longitudinal columns do overlap. It will be recognized that other arrangements of segmented terminals, including any of those arrangements described above with respect to arrangements of segmented electrodes, can be used.

The connector 844 (FIG. 8C) includes an alignment protuberance 880 that fits in the alignment groove 982 of the lead 903. Engagement of the alignment protuberance 880 of the connector 844 with the alignment groove 982 of the lead 903 ensures that the lead and connector have the proper rotational alignment for correctly coupling the segmented terminals 910 of the lead 903 with the connector contacts 840 of the connector 844. It will be understood that in other embodiments, the alignment groove can be placed on the connector and the alignment protuberance on the lead or other elongate member. It will also be understood that multiple alignment grooves and alignment protuberances can be used.

In the illustrated embodiment, the alignment groove 982 extends into the lead 903 to a central lumen 986 (or stylet lumen) of the lead, as shown in FIG. 9E. In other embodiments, the alignment groove 982 does not extend into the lead 903 as far as a central lumen.

In some embodiments, as illustrated in FIG. 9A, the alignment groove 982 extends between two or more terminals 910 of the lead and may extend between multiple sets 911 of terminals of the lead or even between each of the sets of terminals. In other embodiments, the alignment groove 982 terminates proximal to all of the terminals 910, as illustrated in FIGS. 9B and 9C. Correspondingly, in some embodiments, the alignment protuberance 880 of the connector 844 is disposed only near the entrance of the connector lumen 862 and in other embodiments, the alignment protuberance may extend further along the connector lumen (in some cases, to or near the opposing end of the connector lumen).

Any suitable type of connector contact 840 can be used in connector 844. Examples of suitable connector contacts and connectors can be found in, for example, U.S. Provisional Patent Applications Ser. Nos. 62/077,762 and 62/077,784, both of which are incorporated herein by reference.

Figure 10A:
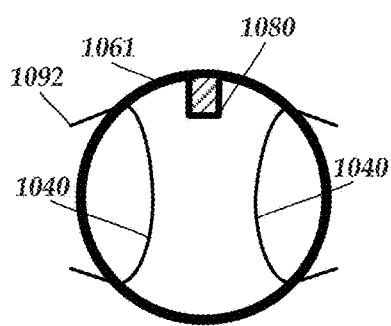
FIG. 10A is a schematic cross-sectional view of one embodiment of segmented connector contacts and a connector lumen, according to the invention.
Figure 10B:
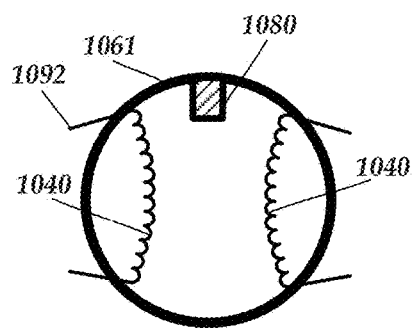
FIG. 10B is a schematic cross-sectional view of another embodiment of segmented connector contacts and a connector lumen, according to the invention.

FIGS. 10A and 10B illustrate, in cross-section, two other embodiments of connector contacts 1040 (two connector contacts are illustrated in each Figure) for use in a connector having a connector wall 1061 that defines the connector lumen 1062 and an alignment protuberance 1080. In FIG. 10A, the connector contacts 1040 are leaf springs 1090 disposed within the connector lumen 1062 with one or more legs 1092 that extend through the connector wall 1061 to make electrical connection (for example, by welding, soldering, or the like) with other portions (for example, conductive members 864 of FIG. 8C) of the connector. In FIG. 10B, the connector contacts 1040 are coiled leaf springs 1091 disposed within the connector lumen 1062 with one or more legs 1092 that extend through the connector wall 1061 to make electrical connection with other portions of the connector.

With respect to leads with the terminal arrays illustrated in FIGS. 8A-9E, the corresponding electrodes can be segmented electrodes, ring electrodes, other electrodes disclosed herein, or any other suitable electrode, or any combination thereof. In particular, although the terminals of a lead may be all or part segmented terminals, the corresponding electrodes may be segmented electrodes, non-segmented electrodes, or any combination thereof.

Figure 11:
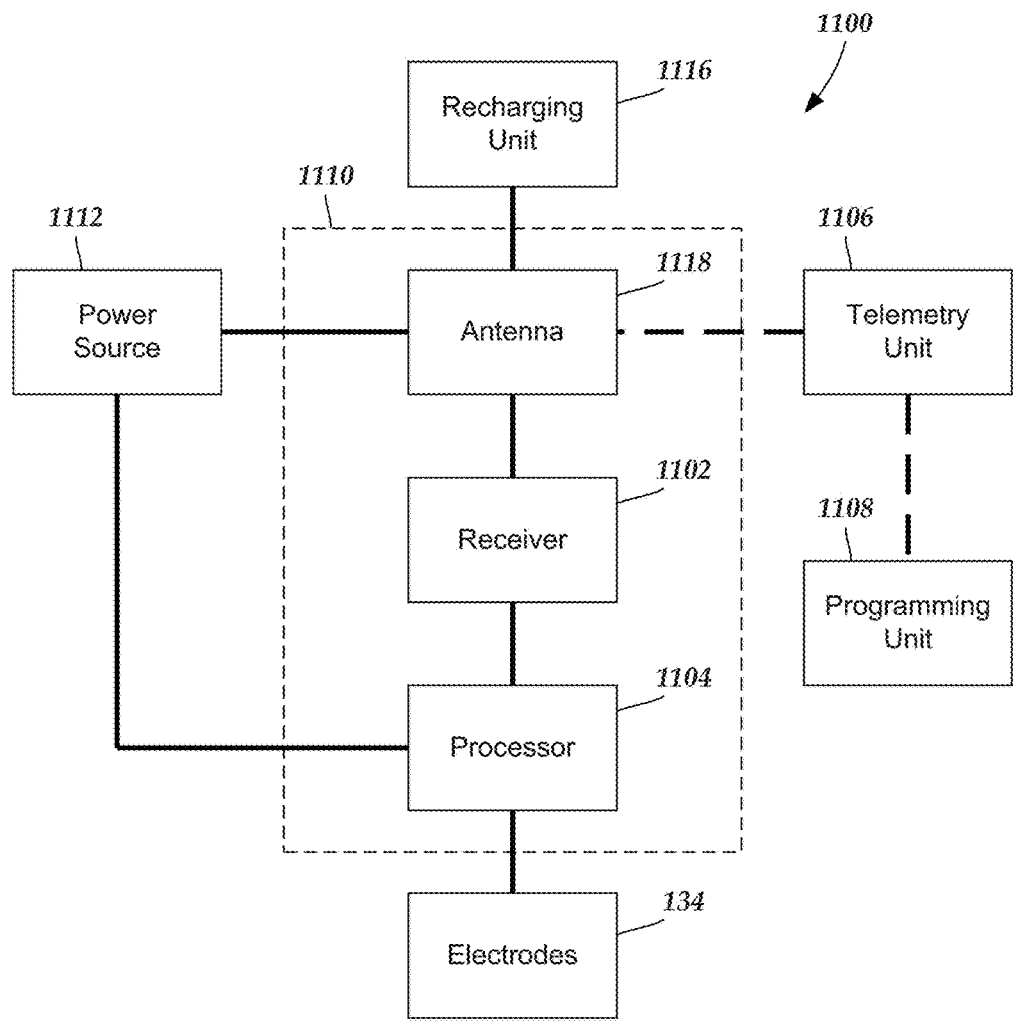
FIG. 11 is a schematic overview of one embodiment of components of an electrical stimulation system, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead comprising:
   a lead body having an outer surface, a proximal end, a proximal portion, at least one distal portion, an outer surface, a perimeter, and a longitudinal length, the lead body defining an alignment groove that begins at the proximal end of the lead body and extends distally, wherein the alignment groove also extends inwardly from the outer surface of the lead body;
   a plurality of electrodes disposed along the at least one distal portion of the lead body;
   a plurality of segmented terminals disposed along the proximal portion of the lead body and arranged in a plurality of sets of segmented terminals, wherein each set of segmented terminals comprises at least two of the segmented terminals disposed in a circumferential arrangement at a same longitudinal position of the lead body, wherein each segmented terminal is exposed on the proximal portion of the lead body to electrically couple to a contact of a connector when the proximal portion of the lead body is inserted into the connector, extends around less than the entire perimeter of the lead body, and is separated from all other segmented terminals by portions of the lead body; and
   a plurality of lead conductors electrically coupling the plurality of electrodes to the plurality of segmented terminals.

2. An electrical stimulation system comprising:
   the electrical stimulation lead of claim 1; and
   a connector defining a connector lumen configured and arranged to receive the proximal end of the lead body of the electrical stimulation lead, wherein the connector comprises a plurality of segmented connector contacts disposed along the connector lumen and arranged in a plurality of sets of segmented connector contacts, wherein each set of segmented connector contacts comprises at least two of the segmented connector contacts disposed in a circumferential arrangement at a same longitudinal position along the connector lumen.

3. The electrical stimulation system of claim 2, further comprising a control module, wherein the control module comprises the connector, a housing, and an electrical subassembly disposed in the housing and electrical coupled to the segmented connector contacts of the connector.

4. The electrical stimulation system of claim 2, further comprising a lead extension, wherein the lead extension comprises the connector.

5. The electrical stimulation system of claim 2, wherein each of the segmented connector contacts comprises a leaf spring.

6. The electrical stimulation system of claim 2, wherein each of the segmented connector contacts comprises a coiled leaf spring.

7. The electrical stimulation system of claim 2, wherein the connector further comprises an alignment protuberance extending into the connector lumen and disposed at least at an opening into the connector lumen, wherein the alignment groove of the lead body is configured and arranged to receive the alignment protuberance to align the lead with the connector.

8. The electrical stimulation lead of claim 1, wherein the alignment groove terminates proximal to any of the segmented terminals.

9. The electrical stimulation lead of claim 1, wherein the alignment groove extends between at least two of the segmented terminals of at least one of the sets of segmented terminals.

10. The electrical stimulation lead of claim 1, wherein the alignment groove extends between at least two of the segmented terminals of each of the sets of segmented terminals.

11. The electrical stimulation lead of claim 1, wherein each of the sets of segmented terminals contains exactly two segmented terminals.

12. The electrical stimulation lead of claim 1, wherein the lead body further defines a central lumen along the lead body and configured and arranged to receive a stylet, wherein the alignment groove extends inwardly from the outer surface of the lead body to the central lumen.

13. An electrical stimulation system comprising:
a connector defining a connector lumen configured and arranged to receive the proximal end of the electrical stimulation lead, wherein the connector comprises
a connector housing containing the connector lumen and defining an opening into the connector lumen,
a plurality segmented connector contacts disposed within the connector housing and along the connector lumen and arranged in a plurality of sets of segmented connector contacts, wherein each set of segmented connector contacts comprises at least two of the segmented connector contacts disposed in a circumferential arrangement at a same longitudinal position along the connector lumen, wherein each of the segmented connector contacts comprises a leaf spring, and
an alignment protuberance extending into the connector lumen and disposed at least at the opening into the connector lumen.

14. The electrical stimulation system of claim 13, further comprising a lead, the lead comprising
a lead body having an outer surface, a proximal end, a proximal portion, at least one distal portion, an outer surface, a perimeter, and a longitudinal length, the lead body further defining an alignment groove extending distally from the proximal end of the lead body and extending inwardly from the outer surface of the lead body,
a plurality of electrodes disposed along the at least one distal portion of the lead body,
a plurality of terminals disposed along the proximal portion of the lead body, and
a plurality of lead conductors electrically coupling the plurality of electrodes to the plurality of terminals.

15. The electrical stimulation system of claim 14, wherein the plurality of terminals is a plurality of segmented terminals disposed along the proximal portion of the lead body and arranged in a plurality of sets of segmented terminals, wherein each set of segmented terminals comprises at least two of the segmented terminals disposed in a circumferential arrangement at a same longitudinal position of the lead, wherein each segmented terminals extends around less than the entire perimeter of the lead body and is separated from all other segmented terminals by portions of the lead body.

16. The electrical stimulation system of claim 15, wherein the alignment groove terminates proximal to any of the segmented terminals.

17. The electrical stimulation system of claim 15, wherein the alignment groove extends between at least two of the segmented terminals of at least one of the sets of segmented terminals.

18. The electrical stimulation system of claim 13, wherein the leaf spring is a coiled leaf spring.

19. The electrical stimulation system of claim 13, further comprising a control module, wherein the control module comprises the connector, a housing, and an electrical subassembly disposed in the housing and electrical coupled to the segmented connector contacts of the connector.

20. The electrical stimulation system of claim 13, further comprising a lead extension, wherein the lead extension comprises the connector.

* * * * *